United States Patent
Chabrol et al.

(10) Patent No.: US 12,011,610 B2
(45) Date of Patent: Jun. 18, 2024

(54) ILLUMINATING DEVICE IMPLANTABLE IN A LIVING BEING

(71) Applicant: Commissariat A L'Energie Atomique et aux Energies Alternatives, Paris (FR)

(72) Inventors: Claude Chabrol, Grenoble (FR); Patrice Caillat, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 17/117,855

(22) Filed: Dec. 10, 2020

(65) Prior Publication Data
US 2021/0178175 A1 Jun. 17, 2021

(30) Foreign Application Priority Data
Dec. 12, 2019 (FR) ...................... 19 14302

(51) Int. Cl.
*A61N 5/06* (2006.01)

(52) U.S. Cl.
CPC ......... *A61N 5/0601* (2013.01); *A61N 5/0618* (2013.01); *A61N 5/0622* (2013.01);
(Continued)

(58) Field of Classification Search
CPC .. A61N 5/0601; A61N 5/0618; A61N 5/0622; A61N 2005/0628;
(Continued)

(56) References Cited

U.S. PATENT DOCUMENTS

| 8,649,836 B2 * | 2/2014 | Shimizu ............. A61B 5/14532 600/316 |
| 2009/0156905 A1 * | 6/2009 | Ries ..................... A61B 5/1459 600/300 |

(Continued)

FOREIGN PATENT DOCUMENTS

| EP | 3 539 449 A1 | 9/2019 | |
| KR | 20160120738 A * | 10/2016 | ............. G16H 20/40 |

(Continued)

OTHER PUBLICATIONS

French Preliminary Search Report dated Jul. 22, 2020 in European Application 19 14302 filed Dec. 12, 2019 (with English Translation of Categories of Cited Documents and Written Opinion), citing documents AA-AD and AO-AP therein, 10 pages.

*Primary Examiner* — Joseph M Dietrich
*Assistant Examiner* — Ranjani Mari Sundaresan
(74) *Attorney, Agent, or Firm* — Oblon, McClelland, Maier & Neustadt, L.L.P.

(57) ABSTRACT

An optically stimulating module to be integrated into a probe is implantable into a living being with a view to locally illuminating a region of said living being. The module includes a casing that is at least partially transparent, and a hermetic electronic unit placed in the casing. The hermetic electronic unit includes an internal volume housing two light sources, a control and processing unit, and a first photodetector. The module also includes a connecting device for connecting the module to a central control and power unit.

19 Claims, 8 Drawing Sheets

(52) U.S. Cl.
CPC ............... *A61N 2005/0628* (2013.01); *A61N 2005/0632* (2013.01)

(58) Field of Classification Search
CPC ........ A61N 2005/0632; A61N 1/36082; A61N 1/36067; A61N 1/0534; A61N 1/0536; A61N 2005/0626; A61N 2005/0612
See application file for complete search history.

(56) References Cited

U.S. PATENT DOCUMENTS

| | | | |
|---|---|---|---|
| 2009/0156912 A1* | 6/2009 | Kuhn | A61B 5/14532 257/E31.127 |
| 2015/0080982 A1* | 3/2015 | Van Funderburk | A61N 1/37247 607/59 |
| 2018/0229041 A1* | 8/2018 | Pepin | A61N 1/36067 |
| 2018/0369606 A1* | 12/2018 | Zhang | A61B 5/4836 |
| 2019/0001149 A1 | 1/2019 | Chabrol et al. | |
| 2019/0053712 A1* | 2/2019 | Rogers | A61B 5/0071 |
| 2019/0060664 A1* | 2/2019 | De Taboada | G02B 6/4298 |
| 2019/0168022 A1* | 6/2019 | Doguet | A61N 1/36135 |
| 2019/0282070 A1 | 9/2019 | Vilhelmsen et al. | |
| 2019/0282077 A1 | 9/2019 | Sørensen et al. | |

FOREIGN PATENT DOCUMENTS

| | | | | |
|---|---|---|---|---|
| KR | 20160120738 A | * | 10/2016 | |
| WO | WO 2017/103380 A1 | | 6/2017 | |
| WO | WO-2018140983 A1 | * | 8/2018 | ......... A61N 1/36125 |

\* cited by examiner

ILLUMINATING DEVICE IMPLANTABLE IN A LIVING BEING

TECHNICAL FIELD OF THE INVENTION

The present invention relates to an illuminating device intended to be at least partially implanted in a living being with a view to illuminating, locally, at least one region of the living being.

PRIOR ART

To treat certain pathologies of a living being, it has been imagined to optically stimulate an internal region of the living being. To this end, devices have been proposed that comprise a light source and that are at least partially or completely implanted in the living being with a view to illuminating the desired region.

The advantageousness of optically irradiating/illuminating certain regions of the human brain with such devices has notably been observed.

However, on account of the risks related to the implantation of such a device in the brain, it will be understood that such a device must be perfectly designed.

Patent application US2017281928A1 and patent application U.S. Pat. No. 10,213,596B2 describe implantable illuminating devices comprising an IPG (acronym of implantable pulse generator) that powers a light source, and a probe comprising a light guide tasked with delivering a light beam to the region to be treated.

Other solutions have also been proposed in the documents referenced US2019/168022A1, EP3539449A1 and WO2017/103380A1.

These solutions do not meet some or all of the following criteria:
illumination at a wavelength tunable from 2 to 50 mm;
compatibility of an illumination source with IPGs available on the market (i.e. without hardware modification); and
modularity (ability to stimulate electrically and/or optically, choice of a plurality of illumination wavelengths, etc.).

Moreover, it is known that the curve of treatment effectiveness is a bell-shaped curve depending on the duration of the treatment and on the injected optical power.

At the present time, there are no simple and compact solutions allowing the effectiveness of such a treatment to be measured.

The aim of the invention is to provide an implantable, optically stimulating device configured to meet one or more of the aforementioned objectives, i.e.:
compactness and suitability for deep brain stimulation (DBS);
compatibility with existing IPGs;
modularity and adaptability (electrical and/or optical stimulation and choice of the illumination wavelength);
therapeutic effectiveness, achieved by tracking biological parameters via characterization of the surrounding medium (optical, thermal, electrical method); and
ability to monitor correct operation of the probe.

Moreover, the solution of the invention will possibly allow the following objectives to be met:
evaluation of the penetration of the light into the tissues, in order to adjust the dose applied to the patient;
multi-wavelength stimulation;
assistance with surgical placement, by recording absorption/scattering parameters during the insertion of the probe into the biological tissues; and
surveillance of the variation in the optical parameters of surrounding tissues via various methods (DRS for diffuse reflectance spectroscopy, fluorescence, absorption peaks of biological molecules, and/or thermal tracking).

The solution of the invention will be implemented based on materials recognized to be biocompatible.

DISCLOSURE OF THE INVENTION

This aim is achieved via an optically stimulating module to be integrated into a probe that is implantable into a living being with a view to locally illuminating a region of said living being, said module comprising:
a casing that is at least partially transparent,
a hermetic electronic unit that is placed in said casing and that comprises an internal volume housing a light source, a processing and control unit, a first photodetector and a second photodetector, an opaque screen separating its internal volume into a first space containing the light source and the second photodetector, and a second space containing the first photodetector, and
a connecting device for connecting said module to a central control and power unit.

According to one particularity, the module comprises an optical filter for selecting wavelengths applied to said first photodetector.

According to another particularity, the module may comprise at least one waveguide arranged on the first photodetector with a view to limiting any parasitic light and to optimizing a capture of photons.

According to another particularity, the module comprises a transparent porthole, chosen to capture signals of wavelength longer than 4 µm.

According to another particularity, the electronic unit comprises at least one substrate comprising two opposite faces, said two light sources being mounted on a single of the two faces of said substrate.

According to another particularity, the electronic unit may comprise a suitable hermetic cover on the substrate and forming said internal volume of the electronic unit.

According to another particularity, the casing of the module may comprise a ring that is closed at its two ends by two plugs, said two plugs bearing means for holding the electronic unit housed in the casing.

According to another particularity, the module may comprise electrically stimulating electrodes on the lateral surface of its ring.

According to another particularity, the module may comprise a coating material injected into its casing around the hermetic electronic unit.

The invention also relates to a probe that is implantable into a living being, said probe being intended to be electrically connected to an electrical power source and having an elongate architecture, said probe comprising a plurality of optically stimulating modules such as defined above, said modules being juxtaposed along the probe and separated from one another by a nonzero distance, and said probe comprising a coating material filling the space between two adjacent modules.

The invention also relates to an implantable illuminating device intended to be implanted into a living being with a view to locally illuminating a region of said being, said device comprising an electrical power source comprising a plurality of parallel electrical supply paths and a probe that is electrically connected to the electrical power source and that has an elongate architecture between a proximal end and a distal end, and said device comprising a probe such as defined above.

According to one particularity, the power source is an implantable pulse generator.

According to another particularity, the device comprises means for determining a light dose to be applied depending on received signals coming from one or more first photo-detectors of the modules.

BRIEF DESCRIPTION OF THE FIGURES

Other features and advantages will become apparent in the following detailed description that is provided with reference to the appended drawings, in which.

DETAILED DESCRIPTION OF AT LEAST ONE EMBODIMENT

Figure 1:
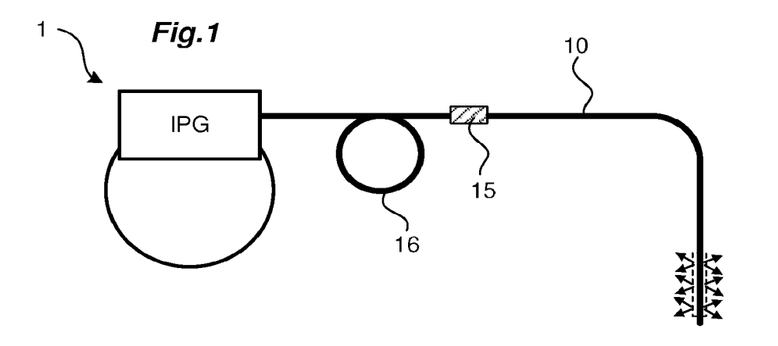
FIG. 1 shows an example of an embodiment of the device according to the invention.

The invention relates to an implantable illuminating DBS device 1 (DBS being the acronym of deep brain stimulation). This device notably allows localized illumination (for example in the near infrared or with any other wavelength depending on the envisioned treatment—neuroprotective treatment, optogenetic treatment, etc.) of target tissues (for example the SNc, hippocampus, striatum, etc.) to be carried out while minimizing the medical risks of the implantation. This device may in particular be used to treat neurodegenerative diseases such as Parkinson's disease, Alzheimer's disease, Huntington's disease, etc.

It will be seen that the device 1 may optionally incorporate solutions enabling other modes of stimulation (notably electrical stimulation).

The illumination of the tissues may have various objectives depending on the application: neuroprotection, optogenetics, stimulation, etc. A number of targets are concerned, for example: the substantia nigra pars compacta (SNc), which degenerates in Parkinson's disease; the hippocampus, main center implicated in the start of Alzheimer's disease; and the striatum for Huntington's disease. The illumination may be delivered directly to the tissues (bidirectional illuminator, this surgical strategy involves risks of additional lesions) or via routes passing through the ventricles (cavities allowing cerebrospinal fluid (CSF) to circulate) and making contact with the structures to be treated (directional illuminators).

Moreover, the device also allows measurements to be taken with a view to performing various diagnostics on and monitoring the surrounding tissues. The device allows correct individual operation of the light sources to be monitored with a view to guaranteeing correct treatment.

The device 1 of the invention comprises an electrical power source. This power source is advantageously composed of an implantable pulse generator (commonly called an IPG) referenced IPG in the drawings.

Figure 2A:
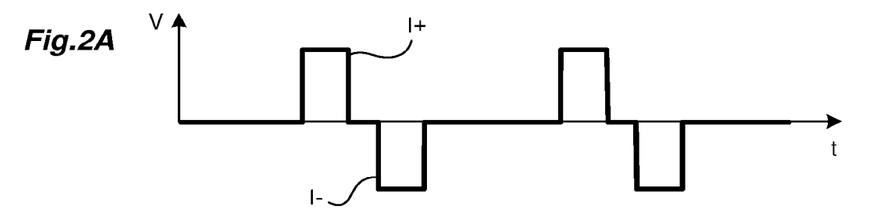
FIGS. 2A and 2B illustrate various types of stimulation current or voltage signals able to be generated by the generator employed in the device of the invention.
Figure 2B:
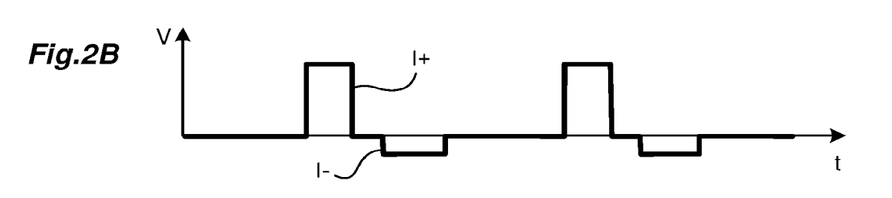

As known, an implantable pulse generator mainly comprises a circuit board and a battery, which may or may not be rechargeable. The circuit board comprises a microcontroller that is responsible for managing the operation of the generator. The IPG may especially be programmed to deliver what are referred to as bipolar pulses, such as those shown in FIGS. 2A and 2B. In FIGS. 2A and 2B, the waveform thus comprises a positive square pulse I+ and a negative square pulse I−, which are separated from each other by a dead time. To balance the electrical charges injected into the tissues, the two pulses may be symmetric (as illustrated in FIG. 2A) or modulated in amplitude and in duration (as illustrated in FIG. 2B) with the same amount of charge injected during both pulses (t×i×V with t the duration of the pulse, i current and V voltage). The generator comprises n paths, with n higher than or equal to 2, and for example between 4 and 12 paths.

Figure 2C:
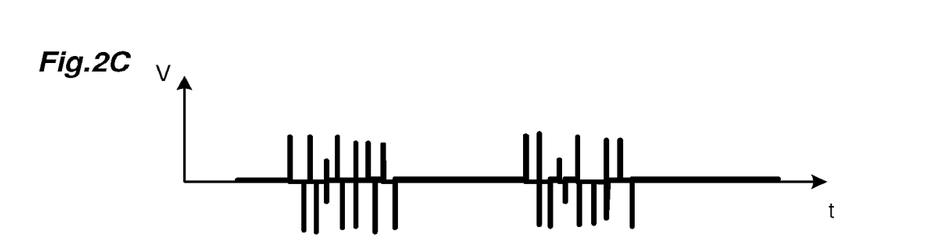
FIG. 2C illustrates an example of pulsed signals serving for implementation of impedance monitoring.

FIG. 2C shows the IPG-generated signals that allow the impedance of the probe 10 that is connected thereto to be monitored. These signals may be coded in order to individually address each function of each of the electronic units 3.

The device 1 then comprises an implantable probe 10 connected to the generator.

This implantable probe 10 takes the form of a supple elongate stem. The probe 10 advantageously has a circular cross section. By way of example, the diameter of the cross section of the probe may range from 1 to 3 mm, and is preferably 1.3 mm in order to be compatible with the standard tools used in DBS.

The device 1 comprises electrically connecting means allowing the probe 10 to be connected to the IPG via its proximal end, by way of a connector 15 and an extension 16. At the distal end, the probe 10 advantageously has an atraumatic shape 100 (for example an oblong or spherical shape).

According to the invention, over at least some of its length, the probe 10 incorporates a plurality of juxtaposed optically stimulating modules M forming a strip. This strip is advantageously located in proximity to the distal end of the probe 10.

The number of modules of the probe 10 may be tailored to the pathology to be treated and to the size of the region of tissue to be treated (which may for example range from 5 to 50 mm in length).

Figure 3:
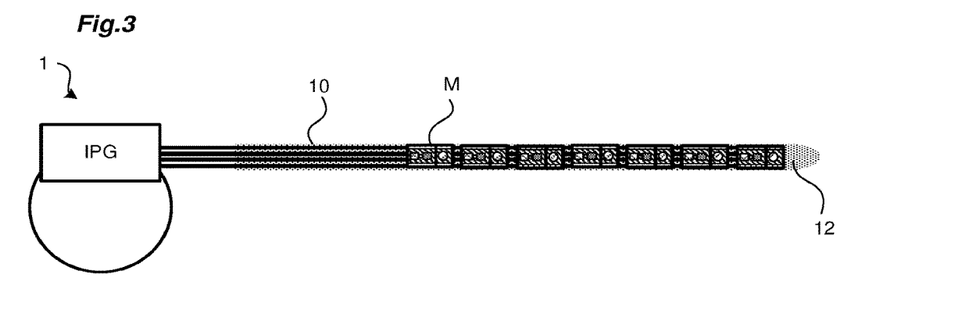
FIGS. 3 and 4 schematically show the architecture of the device according to the invention, FIG. 4 being a close-up of the probe of the device.
Figure 4:
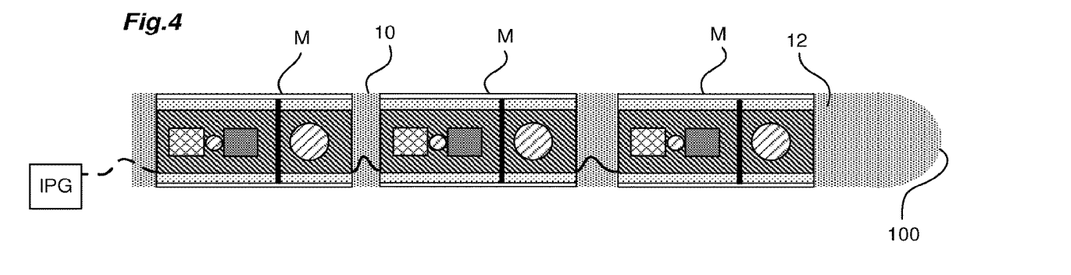

With reference to FIGS. 3 and 4, the modules M are connected to one another so as to form a daisy chain and are held together by a coating material 12 such as silicone, polyurethane or epoxy, the material possibly being chosen notably depending on the rigidity required for the application. Each module M Is connected to the IPG by a point-to-point link. It will be seen below that the point-to-point link incorporates a plurality of conductors, which are required for the module to operate.

With reference to FIGS. 5A to 5C and 6A to 6C, each optically stimulating module M may comprise a casing 2. The casing 2 may comprise a ring made of a transparent and biocompatible material such as sapphire or silica and closed at its two ends by plugs (not shown), so as to form a hollow cylinder incorporating an electronic unit notably equipped with an optical unit. The cylinder may have an outside diameter of 1300 μm.

The two plugs are used to correctly position the electronic unit and to facilitate filling of the cavity with a coating material 22, which may be a transparent or scattering material depending on the sought-after uniformity objective (silicone, polyurethane or epoxy). An epoxy adhesive with a refractive index limiting losses by reflection will possibly be selected, and will possibly be combined with a filler in order to improve heat transfer and seal-tightness, and to meet constraints on expansion during production. In the probe, each module M is thus independent of each other module and has its own electronic architecture, i.e. its electronic unit and its connecting electrical contacts, and its own mechanical architecture, the latter being composed of the ring and plugs. It should be noted that each module of the electronic unit is hermetic, making each module easy to integrate into a probe during its manufacture.

The electronic unit comprises means for storing electrical energy such as a micro-battery or an MOS capacitance or capacitor C1, C2, with a view to supplying the electronic unit 3 with electricity between two supply pulses delivered by the IPG.

The electronic unit of each module M comprises one or more light sources. The light sources may be LEDs, OLEDs, μLEDs, VCSELs, lasers, QCLs, etc. The light sources may be monolithic (such as LEDs) or have a matrix-array arrangement (hybridization of a matrix array of μLEDs the various wavelengths).

The light sources may operate at a voltage lower than a few volts (2 V for example for LEDs), with currents possibly ranging from 2 mA to 25 mA. The IPG may, for its part, deliver a voltage of 15 V and currents ranging from 25 to 50 mA, this for example allowing a plurality of components in series (for example up to seven diodes of 2 V) to be powered.

Nonlimitingly, as shown in the appended figures, each module M comprises two luminous diodes D1, D2. The two luminous diodes D1, D2 may be identical and emit the same wavelength. However, it is also possible to make provision to use two diodes that emit at two separate wavelengths, for example 670 nm for one and 810 nm for the other, with the objective of achieving neuroprotection.

In each module M, light sources other than those used for the optical stimulation and of suitable wavelength may be incorporated in order to allow measurements of surrounding tissues to be taken by measuring backscattered light (DRS, absorption peaks specific to a biological molecule (hemoglobin versus oxyhemoglobin, glucose, etc.). The detectors incorporated into the modules must be able to detect the emission wavelengths of sources.

In each module M, a temperature sensor (for example in CMOS technology) will possibly be incorporated into the electronic module in order to allow the operation of the device to be monitored (thermal safety, in case of heating) and to allow the local temperature of the surrounding tissue to be monitored (this temperature being dependent on the amount of tau protein in the case of Alzheimer's disease for example). A thermally conductive element (for example a finger made of conductive material arranged between the sensor and the casing of the module) may be integrated into the module M to facilitate the measurement of temperature and to make it more reliable.

The illumination is carried out in a plurality of directions that are transverse (and notably radial in a probe of circular cross section) to the axis of the probe. Depending on the modules employed, it is possible to illuminate in various directions, over the entire periphery of the probe or in a narrower defined angular range. It will notably be possible to employ bidirectional illuminating modules (for example 2×110°, standard emission angle of LEDs) or more directional illuminating modules (for example 1×110°).

The electronic unit 3 may comprise a first photodetector PhD1. This first photodetector PhD1 is fastened to the substrate 30 of the electronic unit 3 and is positioned to detect the optical signals transmitted by the surrounding tissues. This first photodetector PhD1 may for example be a hybridized large-area photodiode or a matrix array of CMOS detectors.

The electronic unit 3 may comprise a second photodetector PhD2. This second photodetector PhD2 is fastened to the substrate 30 of the electronic unit and is positioned to monitor correct operation of the luminous diodes. This second photodetector PhD2 may for example be a photodiode in CMOS technology or a hybridized photodiode.

Nonlimitingly, the electronic unit 3 may also comprise any other physical sensor able to participate in biological and physiological monitoring of surrounding tissues, for example a temperature sensor, optical sensor and/or electrical sensor, with the aim of monitoring changes in the surrounding tissue, adjusting the treatment to each patient in each region of illumination (depth of penetration of the light locally into the surrounding tissue) and ensuring the safety of the device.

Figure 5A:
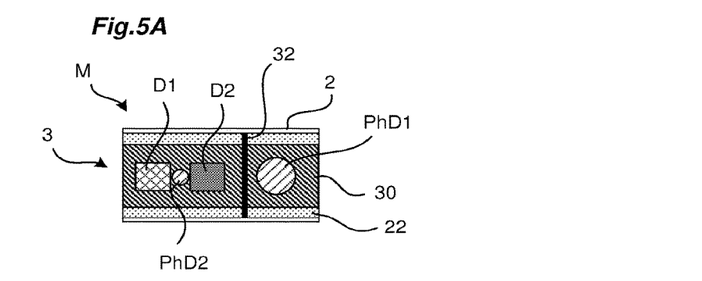
FIGS. 5A to 5C and 6A to 6C schematically show a module according to the invention seen from the side, seen from above and seen along its axis, respectively, according to two different particular embodiments.
Figure 5B:
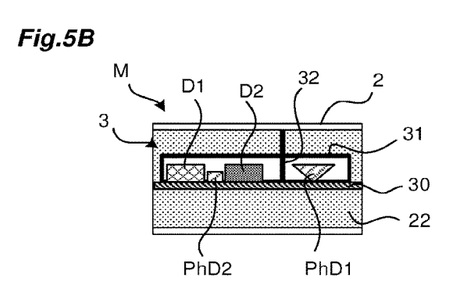
Figure 5C:
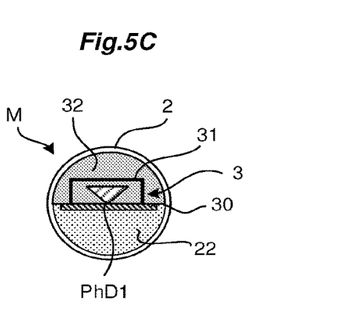
Figure 6A:
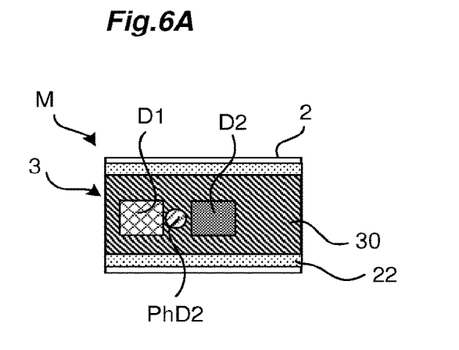
Figure 6B:
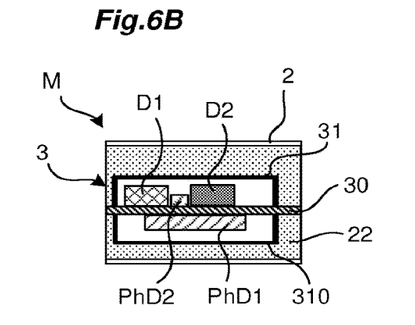
Figure 6C:
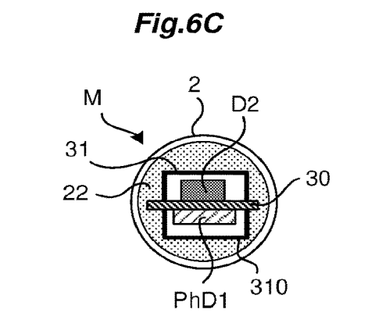

Nonlimitingly, the electronic unit 3 may comprise a substrate 30 having a holding first face (top face) to which the two luminous diodes are fastened. On its top face, the substrate 30 bears the second photodiode PhD2, juxtaposed with the two diodes D1, D2. The latter must be positioned so as to capture some of the radiation emitted by each of the two luminous diodes. The first photodetector PhD1 is separated from the two luminous diodes by a screen in order not to capture the signal emitted by the luminous diodes directly but only the signal transmitted by the surrounding tissues. In the variant of FIGS. 5A to 5C, the first photodetector PhD1 may thus be fastened to said first face, and separated from the two luminous diodes by an opaque screen 32. In the variant of FIGS. 6A to 6C, the first photodetector PhD1 is fastened to the opposite face (bottom face) of the substrate 30, the screen then being formed by the substrate itself.

To make the electronic unit hermetic, a cover 31 is placed on the substrate; this cover 31 will be completely (or locally) transparent.

In the case where the first photodetector PhD1 is fastened to the bottom face of the substrate 30, a second cover 310 may be used to cover the photodiode. As a variant, it is also possible to replace the cover with a conformal deposition deposited, by ALD, on all of the electronic unit, with the exception of the electrical contact-redistribution pads.

Depending on the configuration, nonlimitingly, each substrate 30 may be opaque or at least partially transparent in order to let the light emitted by the luminous diodes pass without inappropriate masking. The layout of the masking due to the conductive tracks and the extent of the transparency of the ring will possibly be tailored to the orientation of the luminous diodes D1, D2 and to the degree of scattering of the light. Each module may thus be configured to create a directional or isotropic illumination.

Figure 14A:
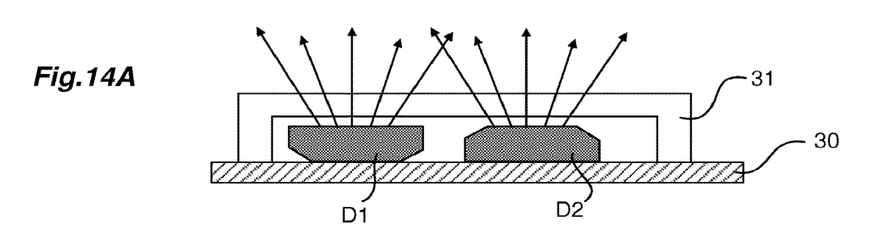
FIGS. 14A and 14B illustrate various illuminating configurations permitted by the device of the invention.
Figure 14B:
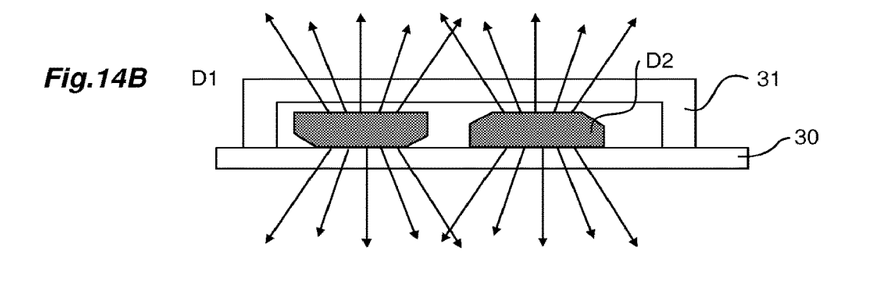

FIGS. 14A and 14B illustrate various possible illumination configurations. In FIG. 14A, the module comprises two diodes fastened to the same face of the opaque substrate 30. The cover 31 is chosen to be transparent. The illumination is thus produced only on a single side. In FIG. 14B, the substrate 30 is transparent and the cover 31 is also transparent, allowing light to be emitted from both sides.

The two luminous diodes D1, D2 are assembled (via conductive adhesive or soldering) and integrated into the hermetic electronic unit 3.

Figure 9:
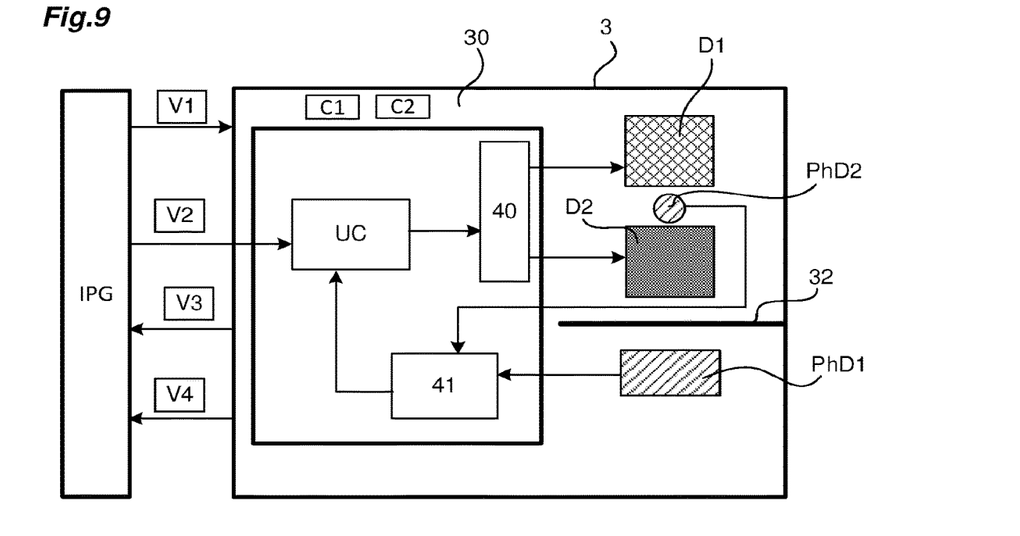
FIG. 9 schematically shows the functional architecture of a module according to the invention.

With reference to FIG. 9, in addition to the components described above, the electronic unit 3 incorporates a control and processing unit UC. This control and processing unit UC may be a CMOS module. It is configured to perform in at least the following functions:
- managing the electrical power supply of the components of the electronic unit 3;
- decoding received input signals;
- regulating the power supplied to the light sources of the module;
- addressing components of the electronic unit 3 and managing the functions;
- conditioning the signals delivered by the photodetectors PhD1, PhD2, the temperature sensor, electrocorticogram (ECoG) electrodes if present, of the electronic unit 3 (integration function, amplification function, current-voltage conversion function, etc.); and
- protecting against electrostatic discharges.

The IPG to which the probe 10 is connected is capable of delivering:
- low-voltage pulses (for example 0.1 V, 40 µsec) in order, for example, to manage the addresses of the modules M and to synchronize the measurements if required; and
- "power" pulses (for example 15 V, 50 mA, 250 psec) for powering the diodes D1, D2, the capacitors C1 and C2 and the electronic unit 3 of each module M.

The IPG incorporates a microcontroller that may perform various functions:
- managing the power supply of the electronic unit 3 of each module M of the probe 10;
- daily programming of the various functions (illumination, type of measurements, signal transfer);
- converting (analog to digital data corresponding to physical values);
- storing the measurements carried out; and
- transferring the data on request.

The IPG will possibly perform a test on each module M, at regular intervals (i.e. programmed intervals or on request), to check it is operating correctly.

With reference to FIGS. 7A to 7F, the module may perform various additional functions, these additional functions possibly of course being combinable with one another.

Figure 7A:
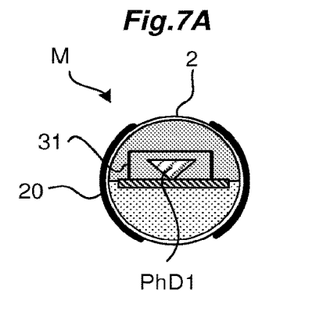
FIGS. 7A to 7G show a plurality of embodiments of the module, seen from the side and seen along its axis.

FIG. 7A:

The module of the invention may be of hybrid type, i.e. comprise optically stimulating means and electrically stimulating means. In this case, as shown in FIG. 7A, the module M, in addition to comprising the luminous diodes D1, D2, also comprises electrodes 20 allowing surrounding tissues to be stimulated electrically. These electrical contacts 20 may be arranged on at least one portion of the surface of the side wall of the cylindrical casing 2 of the module M. The electrodes 20 may be connected to the same IPG as that employed to power the luminous diodes and occupy certain of the specific paths of the generator. The electrodes, which are deposited locally in order to let the optical beam pass, may for example be made of bulk or sputtered platinum-iridium or of IrO2. In FIG. 7A, by way of example, the electrodes 20 are circularly arcuate in cross section and extend over an angular segment of the ring.

When a module is hybrid, i.e. when it possesses both optically stimulating means and electrically stimulating means, it should be noted that it may operate in either of the two stimulating modes or in both stimulating modes simultaneously.

Figure 7B:
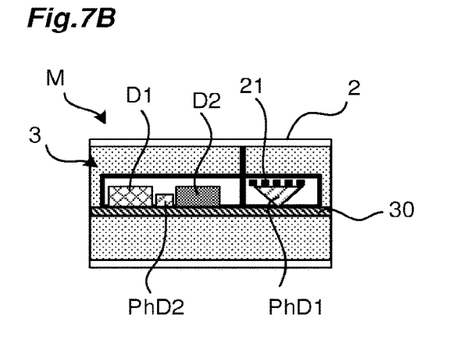
Figure 7C:
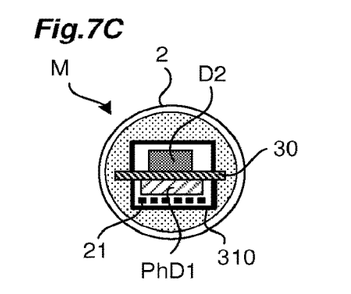

FIGS. 7B and 7C:

The first photodetector PhD1 may be equipped with selective filters 21 (for example dielectric filters) in order to allow measurement of fluorescence (for example amyloid plaques marked with a fluorophore such as "CRANAD-xxx").

Figure 7D:
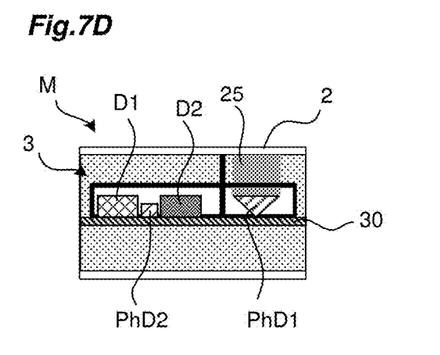
Figure 7E:
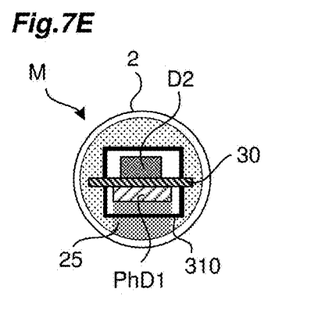

FIGS. 7D and 7E:

The first photodetector PhD1 may be equipped with an optical waveguide 25 to limit parasitic light and to optimize the capture of photons.

Figure 7F:
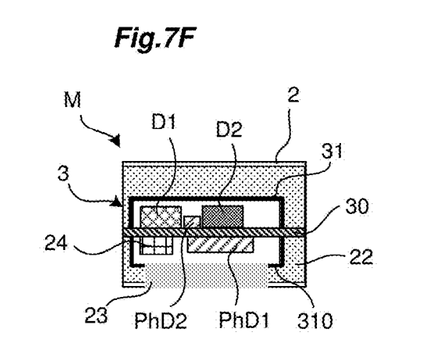
Figure 7G:
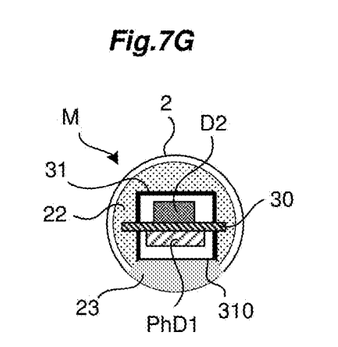

FIGS. 7F and 7G:

The module M may comprise a porthole 23 that is transparent to sources of wavelengths longer than 4 µm. This porthole is made of a material (silicon for example) different from that of its casing 2 (which is for example made of sapphire). The electronic unit may then incorporate a far-infrared (FIR) module 24 for measuring the absorption of the tissues in the wavelength range 4-13 µm.

The control and processing unit UC may comprise analog and/or digital components.

The electronic unit may also incorporate a circuit 40 for driving the two luminous diodes and a circuit 41 for processing the signals delivered by the two photodetectors PhD1, PhD2 and the temperature sensor.

A plurality of paths of the IPG may be reserved for management of the functionalities provided by each module M.

Figure 10:
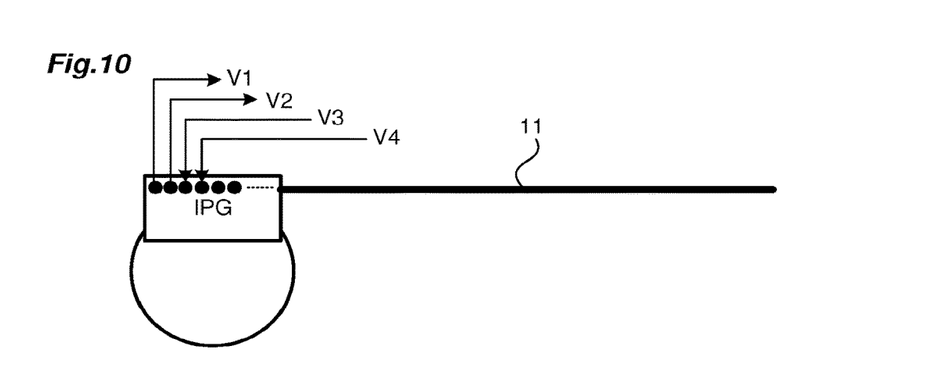
FIG. 10 illustrates the scheme by which a module is addressed by the IPG.

To generate the functionalities of a single module, four conductors (for example) or paths Vx (x ranging from 1 to N paths of the generator) of the IPG are required. With reference to FIG. 10, for each module, the following architecture may be employed:
- a first path V1 is intended for the supply of power to the module: The generator is able to deliver a voltage of about 15 V;
- a second path V2 is intended for addressing the module;
- a third path V3 allows the measurement signals delivered by the module to be collected; and
- a fourth path V4 serves as a voltage reference.

Figures 8A, 8B, 8C:
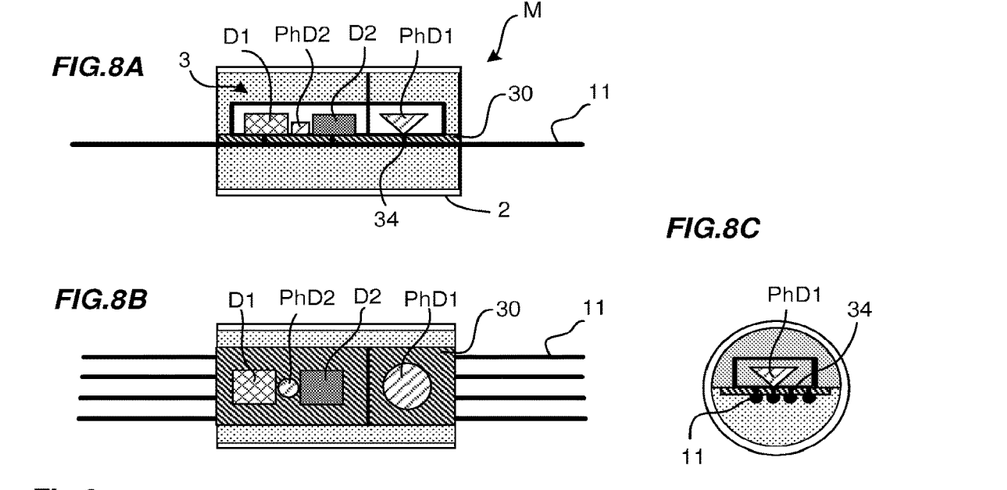
FIGS. 8A, 8B and 8C schematically show a scheme of connection of a module according to the invention to a cable, seen from the side, seen from above and seen in cross section, respectively.

All of the paths of the IPG may be passed through a multistrand cable 11 (4 to 12 paths for example). FIGS. 8A to 8C illustrate a scheme of connection of a module to a multistrand cable 11. The cable 11 may pass through each module M, under the substrate 30, and each electronic component of the module M may be connected to one conductor of the cable using a via 34 produced through the substrate 30.

Figure 11:
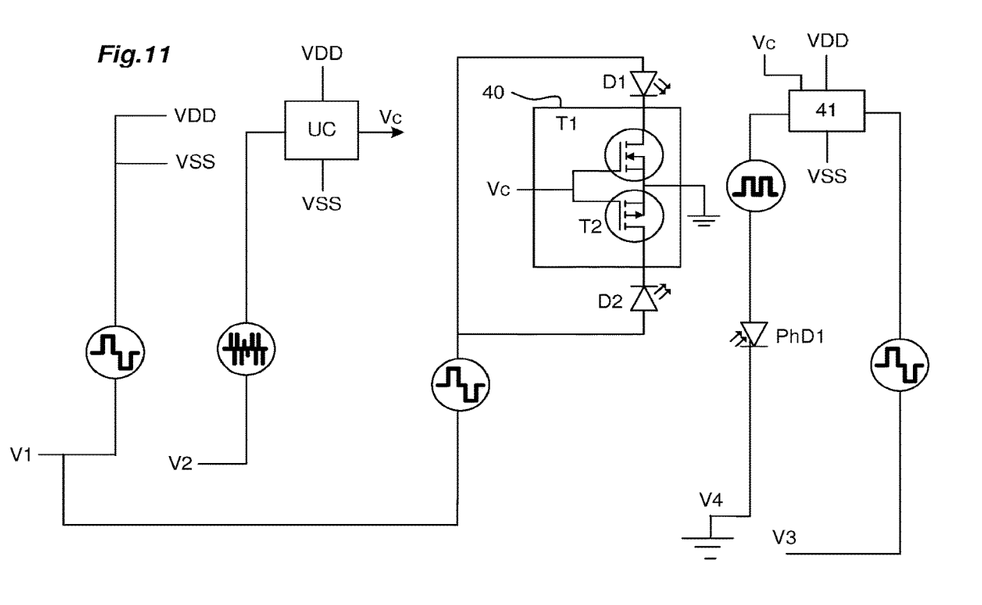
FIG. 11 shows the electronic architecture of the module and the scheme by which the module is electrically connected and addressed.

By way of example, FIG. 11 shows the electronic and operational architecture of an electronic unit employed in the module of the invention. FIG. 11 thus shows:

the first path V1 and the fourth path V4, which are intended to power all of the electronic unit 3 by delivering supply voltages VDD and VSS: the IPG applies a supply voltage (for example 15 V) to this path;

the second path V2, to which the control and processing unit UC is connected and to which control signals may be applied; the control and processing unit UC may comprise a decoder intended to decode the received input control signals. Depending on the received input signals, the control and processing unit UC is configured to generate, as output, with a view to driving the luminous diodes D1, D2, a drive signal Vc intended for the driving circuit 40; the driving circuit 40 may comprise two transistors T1, T2 (MOSFETs for example) that are connected in series with the LEDs, one of these transistors being p-type and the other n-type. Depending on the state of the drive signal Vc (polarity +/−) delivered by the control (IPG) and processing unit UC, and on the positive or negative alternation of the voltage delivered by the supply, the drive circuit 40 turns on the first luminous diode D1 or the second luminous diode D2;

the third path V3, to which is connected at least one photodetector PhD1, which is forward- or reverse-biased depending on the measurement electronics (photovoltaic or photoconductive mode) of the electronic unit 3 and on the processing circuit 41 used to process the signals delivered by this photodetector PhD1; the processing circuit 41 may for example comprise an integrator, a converter or any other component conventionally employed in signal processing. It should be noted that the signals generated by the photodetector PhD2 are processed in the same way. These measurements may be carried out on request, or regularly according to a preestablished protocol stored in the memory incorporated into the generator (IPG). These measurement points may be taken outside of the therapeutic illumination phase.

Figure 12A:
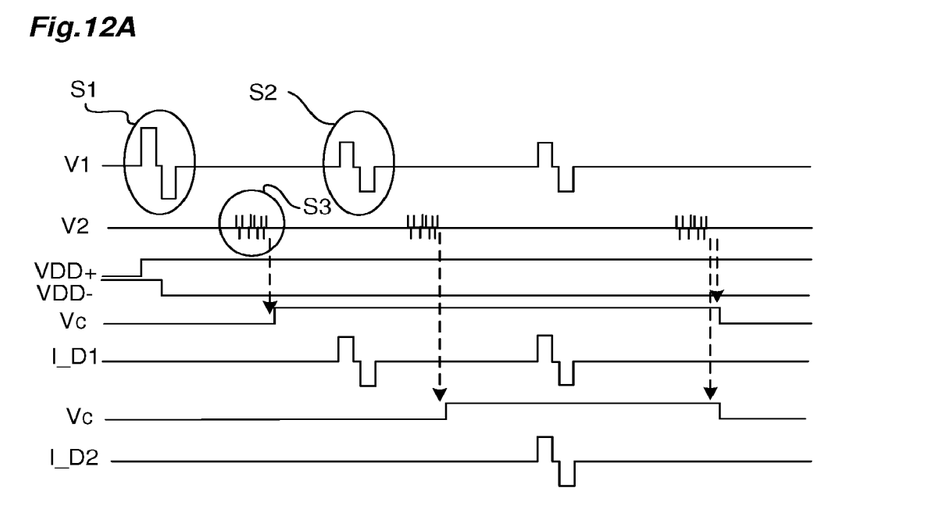
FIG. 12A shows timing diagrams illustrating the principle of a first mode of operation of the device, corresponding to a stimulation achieved by turning on luminous diodes.

FIG. 12A shows timing diagrams illustrating the operation of the device in a stimulating mode, i.e. in a tissue-treating mode. FIG. 12A thus shows:

the supply signals delivered by the generator on its first path V1. First signals S1 are dedicated to supplying power to components of the electronic unit and allow the voltage VDD (VDD+, VDD−) to be delivered. Second signals S2 are dedicated to supplying power to the luminous diodes D1, D2. This supply is driven depending on the state of the drive signal Vc delivered by the control and processing unit UC;

the addressing and control signals S3 delivered by the IPG on its second path. These signals S3 are intended for the control and processing unit UC of the module M. When the module M is addressed, its control and processing unit UC generates drive signals Vc intended for the circuit 40 for driving the luminous diodes;

the current level I_D1, I_D2 passing through each of the two luminous diodes D1, D2, after control thereof.

Figure 12B:
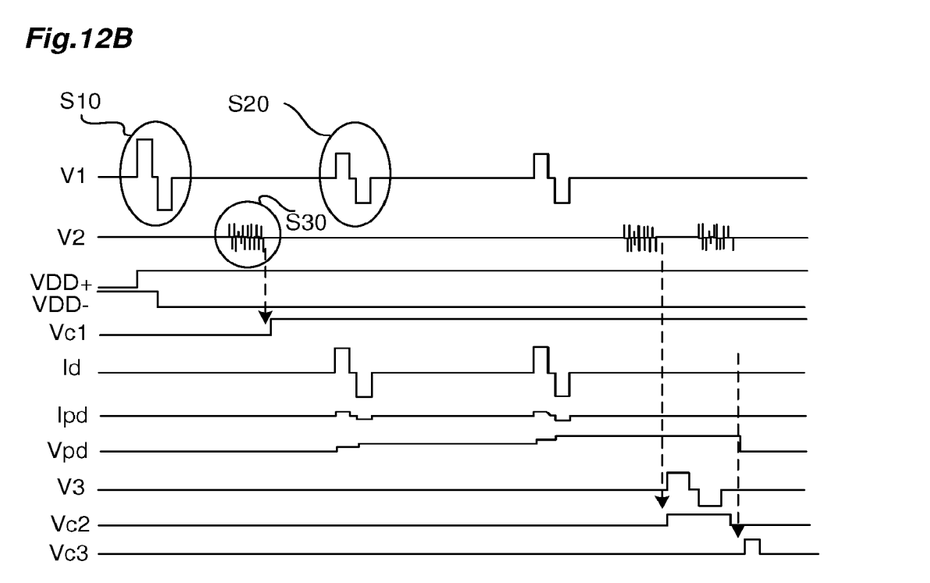
FIG. 12B shows timing diagrams illustrating the principle of a second mode of operation of the device, corresponding to signals measured by a photodetector of the module being read after turn-on of the luminous diodes.

FIG. 12B shows control and measurement timing diagrams illustrating the operating principle of the device in a measuring mode. FIG. 12B thus shows:

the supply signals delivered by the generator on its first path V1. First signals S10 are dedicated to supplying power to components of the electronic unit and allow the voltage VDD (VDD+, VDD−) to be delivered. Second signals S20 are dedicated to supplying power to the luminous diodes D1, D2. This supply is driven depending on the state of the drive signal Vc delivered by the control and processing unit UC;

the addressing and control signals S30 delivered by the IPG on its second path. These signals S30 are intended for the control and processing unit UC of the module M. When the module M is addressed, its control and processing unit UC generates drive signals Vc (Vc1, Vc2 and Vc3 in our example) intended for the driving circuit 40 of the luminous diodes D1, D2;

the current level Id passing through each of the luminous diodes D1, D2, after control thereof with Vc1;

the current signal Ipd measured on the output of the photodetector PhD1 after command thereof with Vc2;

the voltage signal Vpd obtained on the output of the processing circuit 41;

the voltage signal that is read on the third path V3 by the IPG;

the reset of the photodetector and of the integrator after reception of the control signal Vc3.

Figure 13:
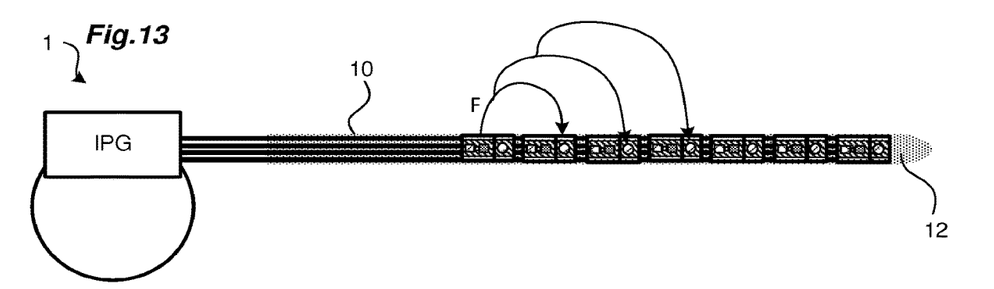
FIG. 13 illustrates the measuring principle employed to adjust the optical dose using the device of the invention.

It should be noted that the device according to the invention, equipped with a plurality of modules such as described above, will be able to perform various treatments or various functions:

adjustment of the optical dose: A treatment sequence comprises controlling a first module of the probe into optically stimulating mode so as to cause emission of a light beam F and measuring the signals transmitted by the tissues to the other modules of the probe (see FIG. 13). This sequence may be repeated for each module of the probe. Such measurements allow the generator to determine the depth of penetration of the light and thus the absorption/scattering coefficients of the surrounding tissues, with a view to adjusting the dose of light to be emitted depending on the results of the measurements. Such measurements may be carried out at regular intervals or in real-time, via use of an automatic-control loop. The measurement taken by the first photodetector PhD1 of each module is proportional to the depth of light penetration;

various biological effects to be monitored:
micro-vascularization, with a view to evaluating the level of scarring and/or changes in surrounding tissues;
temperature, notably useful in case of Alzheimer's disease;
monitoring of the density of amyloid plaques in the hippocampus; DRS measurement with suitable wavelengths allows any changes in the surrounding tissues to be observed;
monitoring of StO2 (cerebral tissue oxygen saturation);
detection of amyloid plaques via measurement of fluorescence induced by a fluorophore such as CRANAD-xxx.

The invention thus has many advantages. An implantable optically stimulating device that is "multiplexable" by virtue of its control and processing unit UC and that allows surrounding tissues to be monitored by virtue of the use of a photodetector, is provided.

The advantage of providing an illuminating probe that is directly implanted into or that makes contact with the structures to be treated is that it allows changes in biological parameters to be observed directly in the tissues in question via an optical measurement (DRS, amplitude pulsation, StO2, etc.). Various 650 to 1070 nm light sources are known to be effective in the treatment of neurodegenerative diseases. The same wavelengths are perfectly suitable for measuring vascularization, O2 saturation, and absorption and scattering in cerebral tissues.

This device moreover allows the optical parameters of the tissues to be recorded during the placement of the probe. In particular:
- optical parameters may be measured (absorption and scattering by DRS measurement) at various wavelengths in order to optimize the dose applied to the patient during stimulation;
- tissues may be located, via a simple measurement of reflectivity, in order to assist with deep placement of the probe (for example, in the case of Parkinson's disease, electrodes are placed in the STN to compensate for the lack of dopamine and the probe extends 5 to 10 mm to illuminate the SNc, center targeted by NIR treatment); and
- micro-hemorrhages may be monitored during the descent of the probe.

The device is compatible with the use of a conventional IPG. It is moreover particularly compact, suitable for deep surgery and may prove to be particularly adaptable because of the ability to stimulate both optically and electrically.

Furthermore, it should be noted that the device may be manufactured using standard technologies:
- CMOS technology as regards the electronic unit;
- LED, OLED, µLED, VCSEL or other laser technology as regards the diodes;
- photodetector made of silicon or a matrix array of CMOS photodiodes;
- ring- or strip-shaped metal electrodes; and
- hermeticity by laser welding of the cover and/or atomic layer deposition (ALD) on components of the electronic unit.

The invention claimed is:

1. A probe that is implantable into a living being, said probe being intended to be electrically connected to an electrical power source and having an elongate architecture, wherein said probe includes a plurality of optically stimulating modules, each of the modules comprising:
   a casing that is at least partially transparent,
   a connecting device for connecting said module to a central control and power unit,
   a hermetic electronic unit that is placed in said casing and that comprises an internal volume housing a light source, a control and processing unit, a first photodetector and a second photodetector, and
   an opaque screen separating the internal volume into a first space containing the light source and the second photodetector, and a second space containing the first photodetector,
   said modules being juxtaposed along the probe and separated from one another by a nonzero distance, said probe comprising a coating material filling the space between two adjacent modules.

2. The probe as claimed in claim 1, wherein at least one waveguide is arranged on the first photodetector configured to limit any parasitic light and to optimize capture of photons.

3. The probe as claimed in claim 1, wherein a transparent porthole is chosen to capture signals of wavelength longer than 4 µm.

4. The probe as claimed in claim 1, wherein:
   the electronic unit comprises two light sources, and
   the electronic unit comprises at least one substrate comprising two opposite faces, said two light sources being mounted on a first one of the two faces of said substrate.

5. The probe as claimed in claim 4, wherein the electronic unit comprises a hermetic cover on the substrate and forming said internal volume of the electronic unit.

6. The probe as claimed in claim 1, wherein the casing comprises a ring that is closed at its two ends by two plugs, said two plugs bearing means for holding the electronic unit housed in the casing.

7. The probe as claimed in claim 6, wherein electrically stimulating electrodes are arranged on a lateral surface of the ring.

8. The probe as claimed in claim 1, wherein a coating material is injected into the casing around the hermetic electronic unit.

9. The probe as claimed in claim 1, wherein an optical filter for selecting wavelengths is applied to said first photodetector.

10. An implantable illuminating device intended to be implanted into a living being with a view to locally illuminating a region of said being, said device comprising an electrical power source comprising a plurality of parallel electrical supply paths and the probe as defined in claim 1 that is electrically connected to the electrical power source and that has an elongate architecture between a proximal end and a distal end.

11. The device as claimed in claim 10, wherein the power source is an implantable pulse generator.

12. The device as claimed in claim 10, comprising arranged means for determining a light dose to be applied depending on received signals coming from one or more first photodetectors of the modules.

13. The probe as claimed in claim 1, wherein the first photodetector is configured to detect optical signals transmitted by light emitted from the being and the second photodetector is configured to monitor operation of the light source.

14. The probe as claimed in claim 1, wherein:
   the electronic unit comprises two light sources, and
   the electronic unit comprises at least one substrate comprising two opposite faces, the two light sources and the second photodetector being mounted on a first one of the two faces and the first photodetector being mounted on a second one of the two faces.

15. The probe as claimed in claim 1, comprising a waveguide optically coupled to the first photodetector, disposed in the second space, and configured to direct light from the being to the first photodetector.

16. The probe as claimed in claim 1, wherein the first space and the second space are separated only by the screen in a direction from the first space to the second space.

17. The probe as claimed in claim 1, wherein
   the hermetic electronic unit comprises a cylindrical tube and the internal volume is disposed in an interior of the tube.

18. The probe as claimed in claim 1, wherein the coating material entirely fills the space between the modules.

19. The probe as claimed in claim 1, wherein the screen consists of a single member separating the first space to the second space.

* * * * *